United States Patent [19]
Triplett

[11] Patent Number: 5,906,929
[45] Date of Patent: *May 25, 1999

[54] ENHANCED INOCULANT FOR SOYBEAN CULTIVATION

[75] Inventor: Eric W. Triplett, Madison, Wis.

[73] Assignee: Wisconsin Alumni Research Foundation, Madison, Wis.

[*] Notice: This patent is subject to a terminal disclaimer.

[21] Appl. No.: 08/847,207

[22] Filed: May 1, 1997

[51] Int. Cl.$^6$ .............................. C12N 15/63; C12N 1/21; C12N 15/81; C07H 21/04

[52] U.S. Cl. ..................................... 435/172.3; 435/252.2; 435/252.3; 435/320.1; 536/23.7; 536/24.1

[58] Field of Search .............................. 435/172.3, 252.2, 435/252.3, 320.1; 536/23.7, 24.1

[56] References Cited

U.S. PATENT DOCUMENTS

| | | | |
|---|---|---|---|
| 4,567,146 | 1/1986 | Brewin et al. | 435/172.3 |
| 5,183,759 | 2/1993 | Triplett | 435/252.2 |

OTHER PUBLICATIONS

Sajid et al. Symbiotic activity in pigeon pea inoculated with wild-type Hu-, Hup+, and transconjugant Hup+ rhizobium. Tropical Agriculture. vol. 71(3):182–187, Mar. 1994.

Breil, Brenda T., et al., "DNA Sequence and Mutational Analysis of Genes Involved in the Production and Resistance of the Antibiotic Peptide Trifolitoxin," *Journal of Bacteriology*, pp. 3693–3702 (Jun. 1993).

Evans, Harold J., et al., "Hydrogen Recycling in Nodules Affects Nitrogen Fixation and Growth of Soybeans," pp. 935–942.

Gallie, Daniel R., et al., "Novel High-and Low-Copy Stable Cosmids for Use in Agrobacterium and Rhizobium," 14:171–175 (1985).

Hungria, M., et al., "Relative efficiency, ureide transport and harvest index in soybeans inoculated with isogenic HUP mutants of *Bradyrhizobium japonicum*" *Biol. Fertil. Soils*, 7:325–329 (1989).

Johnson, Erik P., et al., "Plasmid RK2 Toxin Protein ParE: Purification and Interaction with the ParD Antitoxin Protein," *Journal of Bacteriology*, 178(5):1420–1429 (Mar. 1996).

Maier, Robert J., et al., "Toward More Productive, Efficient, and Competitive Nitrogen–Fixing Symbiotic Bacteria," *Critical Reviews in Plant Sciences*, 15(3):191–234 (1996).

Roberts, Richard C., et al., "Definition of a Minimal Plasmid Stabilization System from the Broad–Host–Range Plasmid RK2," *Journal of Bacteriology*, 174(24):8119–8132. Dec. 1992.

Roberts, Richard C., "Characteristics and Significance of DNA Binding Activity of Plasmid Stabilization Protein ParD from the Broad Host–range Plasmid RK2," *The Journal of Biological Chemistry*, 268(36):27109–27117 (Dec. 25, 1993).

Sia, Elaine Ayres, et al., "Different Relative Importance of the par Operons and the Effect of Conjugal Transfer on the Maintenance of Intact Promiscuous Plasmid RK2," *Journal of Bacteriology*, 177(10):2789–2797 (May 1995).

Sobecky, Patricia A., et al., "Characterization of the Stable Maintenance Properties of the par Region of Broad–Host–Range Plasmid RK2," *Journal of Bacteriology*, 178(7):2086–2093 (Apr. 1996).

Weinstein, Michael, et al., "A Region of the Broad–Host–Range Plasmid RK2 Causes Stable in Planta Inheritance of Plasmids in *Rhizobium meliloti* Cells Isolated from Alfalfa Root Nodules," *Journal of Bacteriology*, 174(22):7486–7489, (Nov. 1992).

Triplett, Eric W., et al., "Trifolitoxin Production and Nodulation Are Necessary for the Expression of Superior Nodulation Competitiveness by *Rhizobium leguminosarum* bv. *trifolii* Strain T24 on Clover," *Plant Physiol.*, 85:335–342 (1987).

*Primary Examiner*—Nancy Degen
*Assistant Examiner*—William Sandals
*Attorney, Agent, or Firm*—Quarles & Brady

[57] ABSTRACT

Root nodule bacterial strains are designed specifically to aid in the growth of soybeans. A high copy number plasmid is described to make trifolitoxin, an antibiotic. The plasmid is preferably hosted in a Sinorhizobium species which is capable of nodulating roots of soybean plants. The phenotype of trifolitoxin production confers a competitive advantage on the inoculant strains by inhibiting competitive strains. To facilitate soybean growth a separate hydrogen uptake capability is also included in the inoculant, either in the same Sinorhizobium strain or in a companion trifolitoxin-resistant strain of root nodule bacteria introduced in the same inoculant.

14 Claims, 2 Drawing Sheets

ENHANCED INOCULANT FOR SOYBEAN CULTIVATION

STATEMENT REGARDING FEDERALLY SPONSORED RESEARCH OR DEVELOPMENT

This invention was made with United States government support awarded by the following agencies EPA Award # CR 822882; USDA Hatch Award No. 3853; AGRICCREE Nos. 94-33120-0433, 94-37305-0767. The United States has certain rights in this invention.

CROSS-REFERENCE TO RELATED APPLICATIONS

Not applicable

BACKGROUND OF THE INVENTION

It has been well known for many years that leguminous plants are able to fix nitrogen from atmospheric nitrogen due to a symbiotic relationship between the plant and bacteria which dwell in nodules formed in the roots of the plants. The symbiotic root nodule bacteria are now classified in at least several genera, e.g. Rhizobium, Bradyrhizobium, Sinorhizobium, and Azorhizobium. The three genera of nodule bacteria are characterized in part by the species of legume plant with which they are able to form the symbiotic nodulation relationship. Most of the bacteria which can nodulate soybean are Bradyrhizobium, although Sinorhizobium species can also nodulate soybean roots.

While significant research has been conducted on root nodulation bacteria in the hope of creating bacterial strains which will foster or improve the growth of legume plants cultivated agriculturally, the problem of increasing the effectiveness of inoculants of root nodule bacteria turns out to be a difficult one. In particular, for example, *Bradyrhizobium japonicum* strains now are extent in soils throughout North and South America in those regions in which there has been historic soybean production, even though the species was originally indigenous only to Asia. The existing wild strains are the progeny of bacterial strains originally inoculated into soybean fields but which have now evolved to survive in these soils and climates. The existence of these bacterial strains in the agricultural soil ecosystem is a mixed blessing. These strains of Bradyrhizobium extent in most cultivation areas compete with intentionally inoculated Bradyrhizobium strains for occupation of the nodules of soybean plants, and while the presently extent or native species may be inefficient fixers of nitrogen, they are often superbly adapted for competitive root nodulation in the particular environment or microenvironment in which they now exist and thrive. Accordingly, creating newly improved root modulation bacterial strains which are actually effective in the field as inoculants in increasing crop yields requires considerations of both increasing the effectiveness of the bacteria and also providing the improved or engineered bacteria with a mechanism by which they may compete effectively with bacterial strains now extent in most legume cultivation areas.

One of the characteristics of the nitrogen fixation process as performed by root nodulation bacteria is that a byproduct of the reaction is evolved hydrogen gas. For root nodule bacteria species which evolve hydrogen gas and release it into the atmosphere, a large amount of energy invested in the nitrogen fixation process is lost as the $H_2$ gas is released into the atmosphere. However, it has been found that some diazotroph, or nitrogen fixing, bacteria do not evolve $H_2$ under nitrogen fixation conditions. These bacteria were found to express an uptake hydrogenase enzyme which oxidized the hydrogen to protons and electrons. In the cases of some bacteria, the electron transport initiated by the hydrogenase results in an efficient energy conserving electron transport chain, which results in recovery of most of the energy that would otherwise be lost in hydrogen production.

The multi-gene for hydrogen uptake, designated HUP, was found to exist in several species of root nodulation bacteria. However, many other root nodule bacterial strains and species do not contain this capability, and thus are relatively wasteful in their energy utilization compared to species which have the capability of HUP expression. For example, there are no known HUP positive strains of *Rhizobium etli* or *Bradyhizobium elkanii*. It has also been found that strains of *Bradyhizobium japonicum* which are HUP positive appear to be scarce in agricultural soils.

It has been proposed that the HUP genes can be introduced into root nodule bacteria not natively possessing this phenotype to aid in their agricultural utility. U.S. Pat. No. 4,567,146 discusses one strategy for this approach. However, the potential introduction widespread agronomic potential of uptake hydrogenase phenotype in bacterial strains faces several hurdles. Among them is the fact that the HUP positive inoculant strains must be competitive for modulation with the endogenous strains now present in soils in crop growing areas. The HUP phenotype requires several genes and appears to be a competitive disadvantage in terms of metabolic burden to the bacteria. The second difficulty concerns the fact that there is an inherent instability in the expression of HUP genes in species which do not normally possess these genes. For example, Lambert et al., *Appl. Environ. Microbiol.*, 53:422–428 (1987), were able to engineer hup expression in R. meliloti strains by conjugation of a cosmid clone containing the hup region, from a species of *B. japonicum* which contained the hup region. However, the expression was transient in root nodules because the lack of proper partitioning of the plasmid during cell division in the absence of selection pressure. Addition of tetracycline or other selection antibiotics to commercial inoculants to prevent improper partitioning is expensive, unlikely to be efficient, and could result in modification of animal or soil plant pathogens due to antibiotic resistance, and hence is not practical.

Of course, even if the HUP phenotype can be engineered into a strain of bacteria, there is still the competitiveness problem. One strategy which has been discussed for this problem is to engineer the root nodule bacteria with a toxin which is inhibitory to other root nodule bacterial. U.S. Pat. No. 5,183,759 describes root nodule bacteria engineered to produce trifolitoxin, one such toxin. Conferring a competitive advantage by adding trifolitoxin expression to a root nodule bacteria may not always be practical or effective. For example, it has been found difficult to express trifolitoxin production genes in Bradyrhizobium species. Also, ironically, it has been found that Bradyrhizobium species are several fold more resistant to trifolitoxin than species of *Sinorhizobium fredii*.

In considering the problem of engineering root nodulation bacteria for hydrogenase expression, another issue is the problem of strain by strain engineering of such bacteria. Now that the bacteria originally introduced as inoculants have evolved into discrete strains adapted to fit ecological conditions throughout agricultural regions it may be necessary for competitive reason to engineer different strains of bacteria for new traits for use in different agricultural regions of any given country or region. Accordingly, the ease with which a trait can be transferred among bacterial strains becomes a critical question in the practical use of engineered nitrogen fixing root nodule bacteria for use on field crops.

BRIEF SUMMARY OF THE INVENTION

The present invention is summarized in that a strain of Sinorhizobium fredii is genetically altered for use as a soybean inoculant by the inclusion in the bacteria of a high copy number plasmid conferring upon the bacteria the phenotype of production of trifolitoxin as well as resistance to trifolitoxin. The trifolitoxin production and resistance gene construct is not only included in the bacteria on a high copy number plasmid, the plasmid incorporates a partitioning system within it to ensure that progeny of the bacteria maintain the trait of trifolitoxin production and resistance. Strains of S. fredii can be used as soybean inoculants and are able to nodulate the roots of soybean plants. The trifolitoxin production from such strains will be at such a level as to enable the S. fredii engineered species to successfully compete with native B. japonicum species for nodulation space in the soybean root.

It is another object of the present invention to confer upon the engineered S. fredii species the ability to enhance the energy utilization of the soybean plant by including within the engineered S. fredii bacteria, or in a co-inoculated bacterial strain, a plasmid which includes a genetic cassette capable of expressing the proteins necessary to confer upon the bacterial strain the ability to produce hydrogenase and to recover the energy from hydrogen reduced with the hydrogenase which would otherwise be lost during the nitrogen fixation process The present invention is further summarized in that the improved S. fredii bacterial strain incorporates each of the useful constructs, that for trifolitoxin, and that for hydrogenase construction, on partitioning locus which ensure that the traits will not be lost from the bacterial strain in the field.

Other objects, advantages, and features of the present invention will become apparent from the following specification.

DETAILED DESCRIPTION OF THE INVENTION

Figure 1:
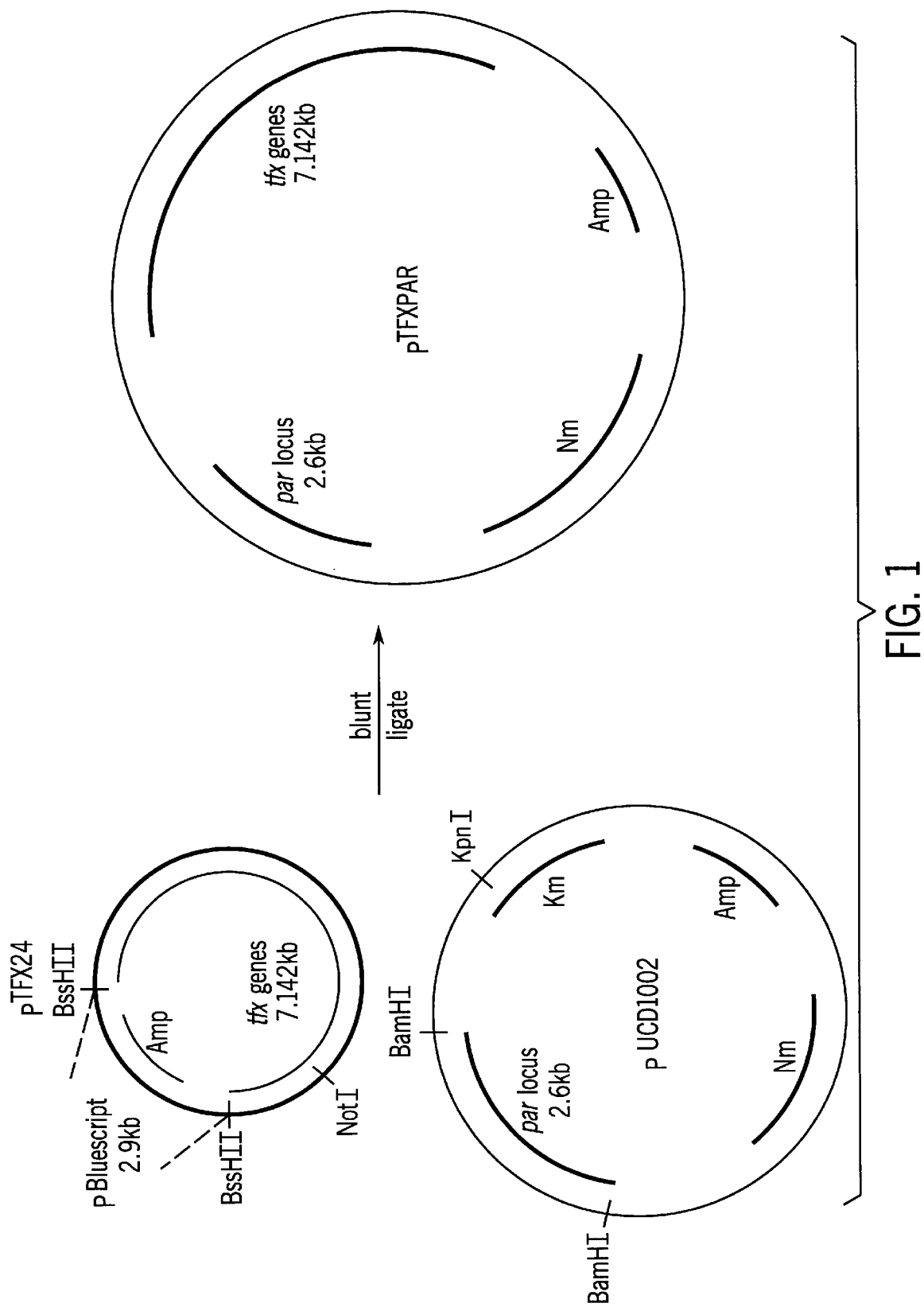
FIG. 1 is a schematic illustration of plasmid manipulation in an example of the present invention.

In accordance with the present invention, a strain of legume associated root nodule bacteria is constructed which has engineered into it the ability to express significant levels of trifolitoxin. The strain is preferably a Sinorhizobium strain if nodulation by this strain is desired but it may also be, as discussed below, a non-nodulating strain. Since trifolitoxin production is necessary at a significantly increased level in order to have a competitive advantage with Bradyrhizobium stains which have greater native resistance to trifolitoxin than do Sinorhizobium strains, the genetic construct to express trifolitoxin is incorporated into the bacteria in a high copy number plasmid engineered to produce several fold more protein than can be produced by a low copy number plasmid harbored by a similar bacteria. To further assist in the inheritance of the trait for trifolitoxin production, the plasmid incorporating the genetic elements for trifolitoxin production and resistance are also provided with a partitioning agent to ensure that plasmids carrying both genetic elements are correctly inherited by progeny of the engineered bacterial strain. A S. fredii strain engineered in the manner described herein is capable of nodulation of soybean roots, and is competitively advantaged to extent Bradyrhizobium strains, due to the production of trifolitoxin at levels which will be toxic to competitive Bradyrhizobium strains.

To facilitate the transfer of the trifolitoxin phenotype into a bacterial strain this most conveniently begins with a plasmid that is stable, exists at high copy numbers in Rhizobium-related species, and already include a partitioning element. One such plasmid, designated pUCD1002, was described by Gallie et al., Plasmid, 14:171–175 (1985). This plasmid includes a par locus from a plasmid known as pTAR, and was designed for use in Agrobacterium and Rhizobium. By "high copy number," as used here, it is intended to refer to a plasmid that exists in five or more copies per cell, and preferably ten or more copies per cell, under normal culture conditions.

Genetic constructs are also available for trifolitoxin production. One construct in that purpose is described in U.S. Pat. No. 5,183,759. The genetic element for the trifolitoxin phenotype must include both trifolitoxin production and resistance to trifolitoxin in order not to harm the host organism. Such genetic element may also be isolated directly from some strains of root nodule bacteria.

A soybean inoculant in accordance with the present invention includes a high copy number plasmid for trifolitoxin production for competitiveness, but may also include a plasmid to assist in soybean plant growth. This second plasmid may be hosted in the same strain or in a second strain included in the inoculant. To confer upon the inoculant the ability to increase the yield of soybean plant, the engineered the second plasmid, intended to aid in the nitrogen fixation process, is for uptake hydrogenase.

Thus, also in accordance with the present invention, an uptake hydrogenase plasmid is constructed which may easily be transferred among various strains of Sinorhizobium or Bradyrhizobium bacteria by conjugation. This uptake hydrogenase plasmid confers upon those bacterial strains harboring the plasmid the ability to increase the effective yield of leguminous plants which form the symbiotic relationship with the root nodule bacteria.

The plasmid in accordance with the present invention achieves this advantage by combining two genetic elements. The first is that the plasmid contains all of the necessary genes in order to express the hydrogen uptake or HUP, phenotype so that the bacteria harboring the plasmid will recover energy from evolved hydrogen which would otherwise be wasted during the nitrogen fixation process. Secondly, the plasmid contains a partitioning element which prevents incorrect partitioning of the plasmid in progeny bacteria thereby ensuring that the presence of the HUP phenotype in daughter bacterial cells is maintained as the bacteria propagates throughout its environment. In this way, stable strains of Sinorhizobium can readily be created which are both competitive and which are capable of enhancing the effective yield from the leguminous plant grown in symbiotic relationship with those bacteria.

Figure 2:
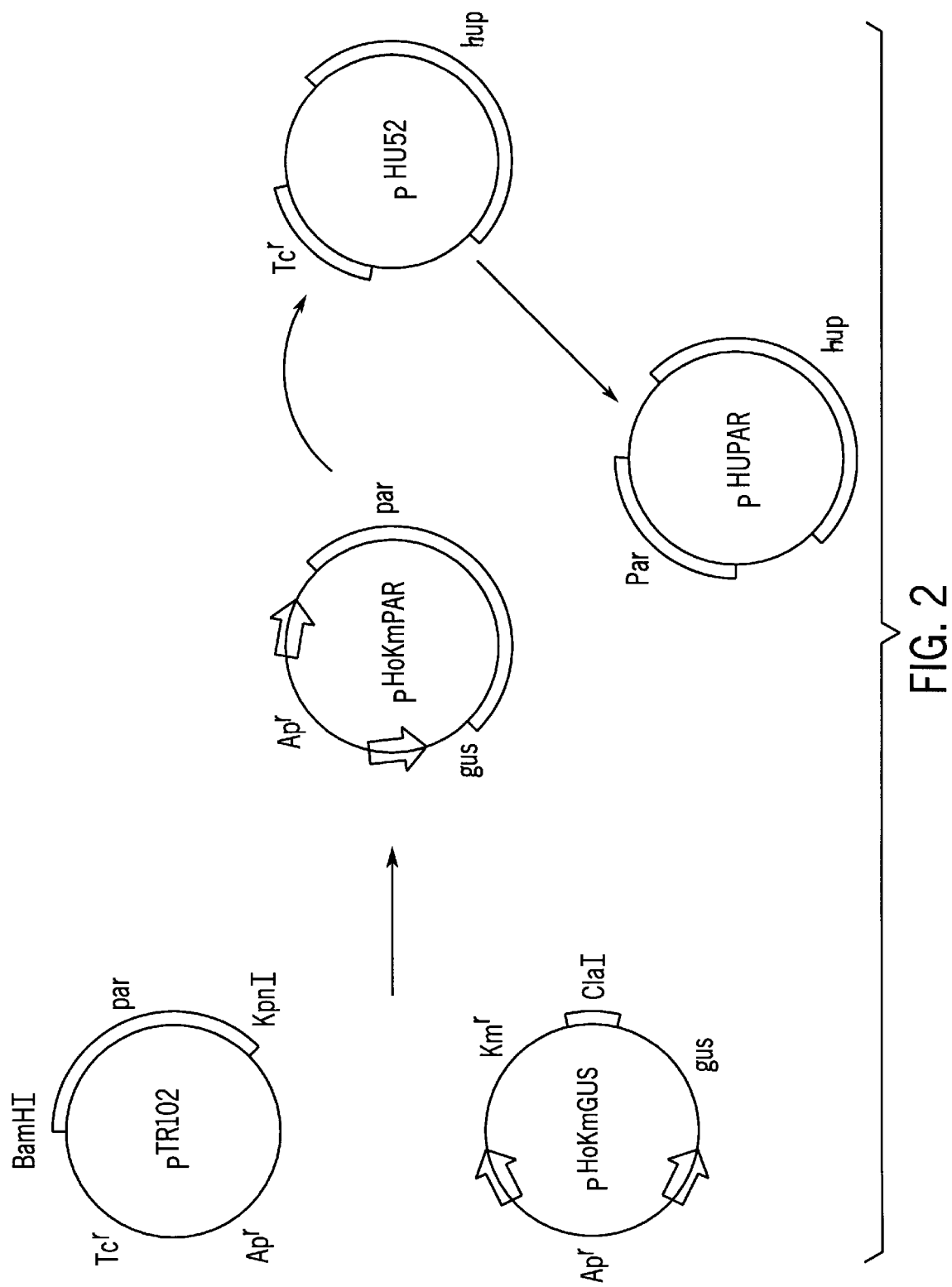
FIG. 2 is a schematic illustration of additional plasmid manipulation s with the plasmid of FIG. 1.

Plasmids incorporating the HUP phenotype have previously been described in the literature. A vector known as pHU52 is described in Lambert et al., *Appl. Environ. Microbiol.*, 53:422–428 (1987). The plasmid HUP pHU52 is a large plasmid containing all of the genes necessary for hydrogen uptake (hup) as well as the genetic sequences necessary to utilize the evolved hydrogen in energy storage in the plant. The problem then simply becomes how to insert the other desired genetic components into this plasmid backbone without disrupting the efficient functioning of the HUP genes. One strategy for accomplishing this objective is to us the tetracycline resistance locus located in pHU52 and direct insertion of foreign DNA into that locus to ensure that none of the genes in the complex HUP operon are disrupted by the insertion. Thus it is more convenient first to combine the other elements desired in the plasmid, specifically the gene cassette encoding trifolitoxin and the resistance to it as well as the partitioning genes, and that genetic cassette may be inserted into the desired locus in the barge pHU52 plasmid using a transposable element.

The partitioning operon for the uptake hydrogenase plasmid is also intended to prevent daughter microbial cells following asexual reproduction of the bacterial strain carrying the plasmid from failing to inherit the desired phenotypes. This par locus is a locus from an *E. coli* plasmid designated RK2 described by Roberts and Helinski in *Jour. Bact*. 174:24:8119–8132 (1992) and Sia et al., *Jour. Bact*. 177:10:2789–2797 (1995). The RK2 par operon contains several genes in at least two operons which has the effect of stabilizing plasmids within a bacteria hosting the plasmid. A plasmid containing the RK2 par locus is exquisitely stable in maintenance during unselected growth due to the presence of the plasmid. Apparently the operon inhibits the growth of plasmidless segregants and thus ensures that all surviving daughter cells contain the entire plasmid into which the par locus is inserted.

The preferred first embodiment of the present invention is a strain of *Sinorhizobium fredii* engineered with two separate plasmids. The first plasmid is a high copy number plasmid conditioning high trifolitoxin production to provide competitiveness. The second plasmid is a HUP plasmid conferring an uptake hydrogenase phenotype to aid in soybean plant growth. A strain of *S. fredii* is preferred as the host for the two plasmids since it has been found that Bradyrhizobium species will not generally express trifolitoxin well and since *S. fredii* strains will nodulate soybean roots. Therefore use of this species permits design of a single strain soybean inoculant that combines competitiveness and nodulation in a single bacterial strain.

It of course a requirement of a plasmid for use in a Sinorhizobium species that the plasmid have a competent application origin and have genetic elements capable of expression in the bacterial host into which the plasmid is inserted. Since all the genetic elements described in the construction of this plasmid come from root nodulation bacteria, with the exception of the par locus, it is not believed that this is a problem. The RK2 par locus has previously been shown to be effective in root nodule bacteria species.

It is conceivable that soybean plants inoculated with the engineered *S. fredii* strain may not provide a yield in field trials comparable to the best *Bradyrhizobium japonicum* strains. If this possibility were to prove true, an alternative strategy within the present invention uses the high copy number trifolitoxin plasmid, like pTFXHCP described below, together with a hydrogen uptake plasmid, but uses the plasmids in separate bacterial strains. It has been previously shown that a non-nodulating trifolitoxin producing strain can limit modulation by trifolitoxin sensitive strains when the strains are mixed in an inoculum with a trifolitoxin resistant strain. Triplett and Barta, *Plant Physiol*., 85:335–342 (1987). Here, the high copy number trifolitoxin producing plasmid would be introduced into a non-nodulating strain in soybean, for example a non-nodulating Sinorhizobium, or a strain of *Rhizobium etli*, and that strain would be used in an inoculum with a strain of trifolitoxin-resistant *Bradyrhizobium japonicum* which hosts a hydrogenase uptake plasmid like pHUPAR described below. The trifolitoxin producing strain in the inoculum would inhibit trifolitoxin sensitive competing strains while the *B. japonicum* strain then occupies the nodules in the roots and fosters the efficient growth of the soybean plants. This strategy thus also combines a high copy number trifolitoxin producing plasmid with the hydrogenase uptake phenotype, it just uses separate bacterial strains to accomplish the same purpose.

EXAMPLE

The construction of the plasmids in accordance with the present invention began with the construction of the high copy number plasmid intended to confer the trifolitoxin phenotype on the Sinorhizobium strain. As illustrated in FIG. 1, the process began by combining two plasmids, PTFX24 and pUCD1002. The plasmid PTFX24 contains a 7.142 kilobase fragment containing the complete sequence as necessary for trifolitoxin production and resistance in transformed host strains. The pUCD1002 plasmid is a high copy number plasmid intended for use in Agrobacterium and Rhizobium hosts. Digest of pTFX24 with Xho I yielded a linearized plasmid containing the complete genetic constructs for the trifolitoxin phenotype. This 10.1 kb insert was then ligated into a 7.6 kb Hind III fragment from the plasmid pUCD1002. Both plasmids were then blunt-ended followed by ligation together. The resulting construct was designated pTFXHLP. The resulting construct exists at a copy number of about 30 per host cell and results in about five fold more trifolitoxin production than achieved with any construct in the past. This construct is capable of conferring significant levels of trifolitoxin production in Sinorhizobium or Rhizobium strains. This is the high copy number plasmid for trifolitoxin production intended to be inserted inside the Sinorhizobium soybean inoculant strain.

To begin the construction of the uptake hydrogenase plasmid, a 32 kb par locus was isolated from the plasmid RK2 described by Weinstein et al. in *J. Bacteriol*. 170:7486–7489 (1992). The par locus from RK2 forces complete plasmid partitioning during cell division by five genes encoded in the plasmid by two divergently transcribed operons. Each of the two operons codes for an independent mechanism to ensure plasmid stability. The first operon, designated parCBA includes a resolvase mechanism while the parDE operon includes a toxin, referred to as parE and antitoxin (parD) mechanism. The par locus confers plasmid stability regardless of the replicon containing the 3.2 kilobase region and has been shown to confer complete plasmid stability with *Sinorhizobium meliloti* during root nodule development.

It was necessary to find a practical way to insert the 3.2 kb par locus into pHU52. It was decided that the most practical way to accomplish this is to insert the par locus within the inverted repeats of a transposon. Then the par locus could be transposed into the tetracycline resistance locus present on pHU52. By providing a transposase in trans, one can insure that the par locus will not transpose out of pHU52 once it has been inserted. In addition, as the Tn3 transposon was chosen for this work also contains a kanamycin resistance gene, it is possible to select for pHU52 after interruption of the tetracycline resistance gene using kanamycin selection. This construction of the transposable par locus has been completed. The transposition of the par locus into pHU52 has been completed.

In FIG. 2 a plasmid designated pTR102 contains the par locus. The plasmid pTR102 was digested with BamHl and KPN1 and a 3.2 kb fragment containing the par locus was recovered. The 3.2 kb fragment was ligated into the blunted unique Cla I site of the plasmid known as pHoKmGUS, as described by Breil et al. *J. Bacteriol*. 178:4150–4156 (1996). The newly created plasmid is called pHoKmPAR, and has a modified Tn3 transposon. The transposon is then used to hop the PAR locus into the tetracycline resistance locus contained within pHU52 using a transposase provided in trans from the plasmid psshe. The resulting combined plasmid designated PHUPAR will confer hydrogen recycling and complete plasmid stability to any bacterium harboring this plasmid. This plasmid pHUPAR can be conjugated into any strain of Sinorhizobium to confer upon that plasmid both increased efficacy as a symbiont as well as enhanced competitiveness for nodule occupancy in the field.

The success of a soybean inoculant incorporating a *Sinorhizobium fredii* strain hosting plasmids like pHV52 and PTFXHCP can be demonstrated by field trials which will show that soybean plants and stands inoculated with such a strain will show increased yield compared to non-inoculated plants or stands.

To assist in the practice of the preferred embodiment of this invention, copies of the plasmids PTFXHCP and pHUPAR have been deposited with the American Type Culture Collection, currently located at 10801 University Boulevard. Manassas. Va., USA, on Apr. 30, 1997, with accession nos. ATCC 98421 and ATCC 98420 respectively. These deposits were under conditions of the Budapest Treaty. Taxonomic descriptions of these deposits are pHUPAR in *E. Coli* C2110 and pTFXHCP in *E. Coli* DH5α.

We claim:

1. A strain of root nodule bacteria comprising:

a recombinant plasmid which encodes trifolitoxin and which has a partitioning locus such that the plasmid is not lost to the bacteria during cell division, the plasmid being present in excess of five copies per cell, wherein said root nodule bacteria produces trifolitoxin in amounts effective to inhibit the growth of *Bradyrhizobium japonicum* competitive root nodule bacteria.

2. A bacteria as claimed in claim 1 wherein the strain is a *Sinorhizobium fredii* strain.

3. A bacteria as claimed in claim 1 wherein the strain is a Rhizobium strain.

4. An inoculant for soybean comprising the bacteria of claim 1.

5. A bacteria as claimed in claim 1 wherein the bacteria also hosts a second plasmid conferring on the bacteria a phenotype of hydrogenase uptake production.

6. A bacteria as claimed in claim 5 wherein the second plasmid also include a partitioning locus.

7. An engineered strain of *Sinorhizobium fredii* bacteria comprising a first plasmid which encodes trifolitoxin and wherein said plasmid also provides resistance to trifolitoxin to the strain and wherein said plasmid has a partitioning locus such that the first plasmid is not lost to the strain during cell division, the first plasmid being present in excess of ten copies per cell, the first plasmid making the strain more competitive on soybean roots than at least one *Bradyrhizobium japonicum* strain that has a native resistance to trifolitoxin in the absence of the first plasmid; and a second plasmid which encodes uptake hydrogenase production and which has a second distinct partitioning locus such that the second plasmid is not lost during cell division, whereby the strain recovers hydrogen evolved during the nitrogen fixation process and uses the hydrogen as a source of energy when nodulating the root of a soybean plant.

8. An engineered strain of *Sinorhizobium fredii* bacteria as claimed in claim 7 wherein the first plasmid includes the trifolitoxin locus from pTFX24.

9. An engineered strain of *Sinorhizobium fredii* bacterial as claimed in claim 7 wherein the partitioning locus in the first plasmid is from pTAR.

10. An engineered strain of *Sinorhizobium fredii* bacteria as claimed in claim 7 wherein the first plasmid is PTFXHCP.

11. An engineered strain of *Sinorhizobium fredii* bacteria as claimed in claim 7 wherein the second plasmid includes the hup+ locus from pHU52.

12. An engineered strain of *Sinorhizobium fredii* bacteria as claimed in claim 7 wherein the second plasmid includes the par locus from an RK2 plasmid.

13. An engineered strain of *Sinorhizobium fredii* bacteria as claimed in claim 7 wherein the second plasmid is pHUPAR.

14. An inoculant for soybean comprising a carrier and the bacteria strain of claim 7.

* * * * *